United States Patent [19]

Blitchington

[11] Patent Number: 4,600,951
[45] Date of Patent: Jul. 15, 1986

[54] SCANNING SAMPLE, SIGNAL GENERATION, DATA DIGITIZING AND RETIMING SYSTEM

[75] Inventor: Frank H. Blitchington, Richmond, Va.

[73] Assignee: AT&T Technologies, Inc., Berkeley Heights, N.J.

[21] Appl. No.: 563,472

[22] Filed: Dec. 20, 1983

[51] Int. Cl.⁴ .................. H04N 1/40; H04N 1/00
[52] U.S. Cl. ............................ 358/280; 358/256; 358/282; 375/118
[58] Field of Search ............ 358/256, 280, 282, 134, 358/140; 360/9.1; 375/118, 122; 370/109; 381/32

[56] References Cited

U.S. PATENT DOCUMENTS

| | | | |
|---|---|---|---|
| 3,702,447 | 11/1972 | Koning | 358/282 |
| 3,795,452 | 5/1974 | Bourdelais | 356/237 |
| 3,835,249 | 9/1974 | Dattilo et al. | |
| 4,152,723 | 5/1979 | McMahon et al. | 358/106 |
| 4,185,298 | 1/1980 | Billet et al. | 358/106 |
| 4,247,873 | 1/1981 | Decuyper | 358/282 |
| 4,272,789 | 6/1981 | Biron | 358/282 |
| 4,298,888 | 11/1981 | Colles et al. | 358/140 |
| 4,336,558 | 6/1982 | Lew | 358/265 |
| 4,338,626 | 7/1982 | Lemelson | 358/93 |
| 4,385,322 | 5/1983 | Hubach et al. | 358/282 |
| 4,408,231 | 10/1983 | Bushaw et al. | 358/282 |
| 4,524,379 | 6/1985 | Okada et al. | 358/140 |

OTHER PUBLICATIONS

Printed Circuit World Expo '80 Proceedings (Nov. 1980) "Automatic Optical Inspection of Printed Wiring Boards", p. 44 by Warren M. Sterling, Palo Alto Resear. Ctr.
Automatic Inspection System for Printed Circuit Photomarks, a product circular by Fujitsu, Ltd. (published by early 1983).
Restrick, R. C. "An Automatic Optical Printed Circuit Inspection System," Solid State Imaging Devices, SPIE, vol. 116, Bellingham, Washington, Aug. 23-24, 1977. pp. 76-81.

Primary Examiner—James J. Groody
Assistant Examiner—John K. Peng
Attorney, Agent, or Firm—W. G. Dosse; S. I. Rosen

[57] ABSTRACT

A system for generating a substantially-continuous stream of binary signals representative of the presence of copper on the surface of a fluorescent, substrate of a board. A beam is swept by mirror facets of a rotating mirror drum along a path on the board. When the beam strikes copper it is merely reflected. When the beam strikes the substrate, a fluorescence is produced. The resultant light is gathered by cylindrical lenses and fiber optic bundles. The color of the light is blocked by filters and the fluorescence color energizes photomultiplier tubes. A threshold setting and sensing circuit senses the output of the photomultiplier tubes and controls their bias voltage to produce a constant level of output from fluorescence and then produces a stream of binary signals that are representative of the presence/absence of copper on the surface of the board. The swept beam is split to send a portion of its energy through an optical grating. The intermittent light passing through the optical grating is gathered by a fiber optic bundle and is sensed by a photomultiplier tube. The output of the photomultiplier tube is doubled in frequency and used to sample and store the binary signals in the memory of a scanning converter. The binary signals arrive in short bursts of higher-frequency signals separated by periods of absence of binary data. The binary signals stored in the scanning converter are then read out substantially continuously for subsequent processing at a lower frequency.

8 Claims, 5 Drawing Figures

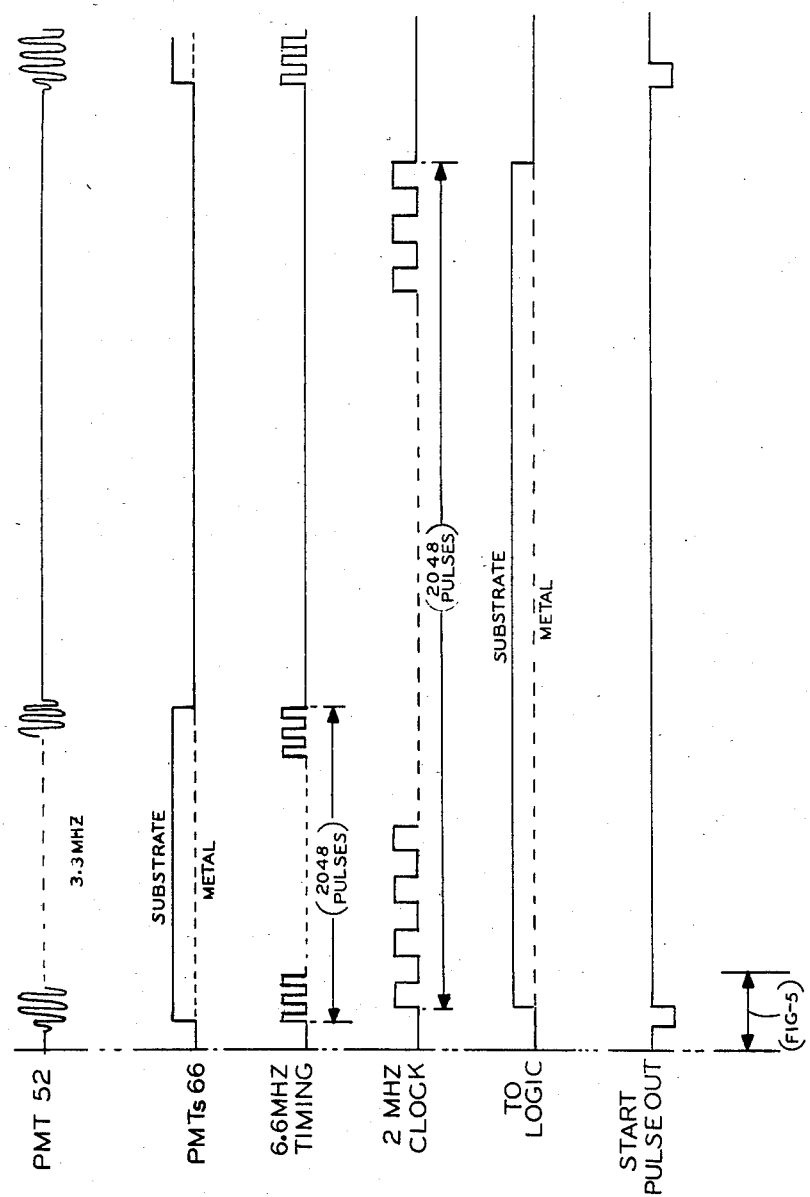

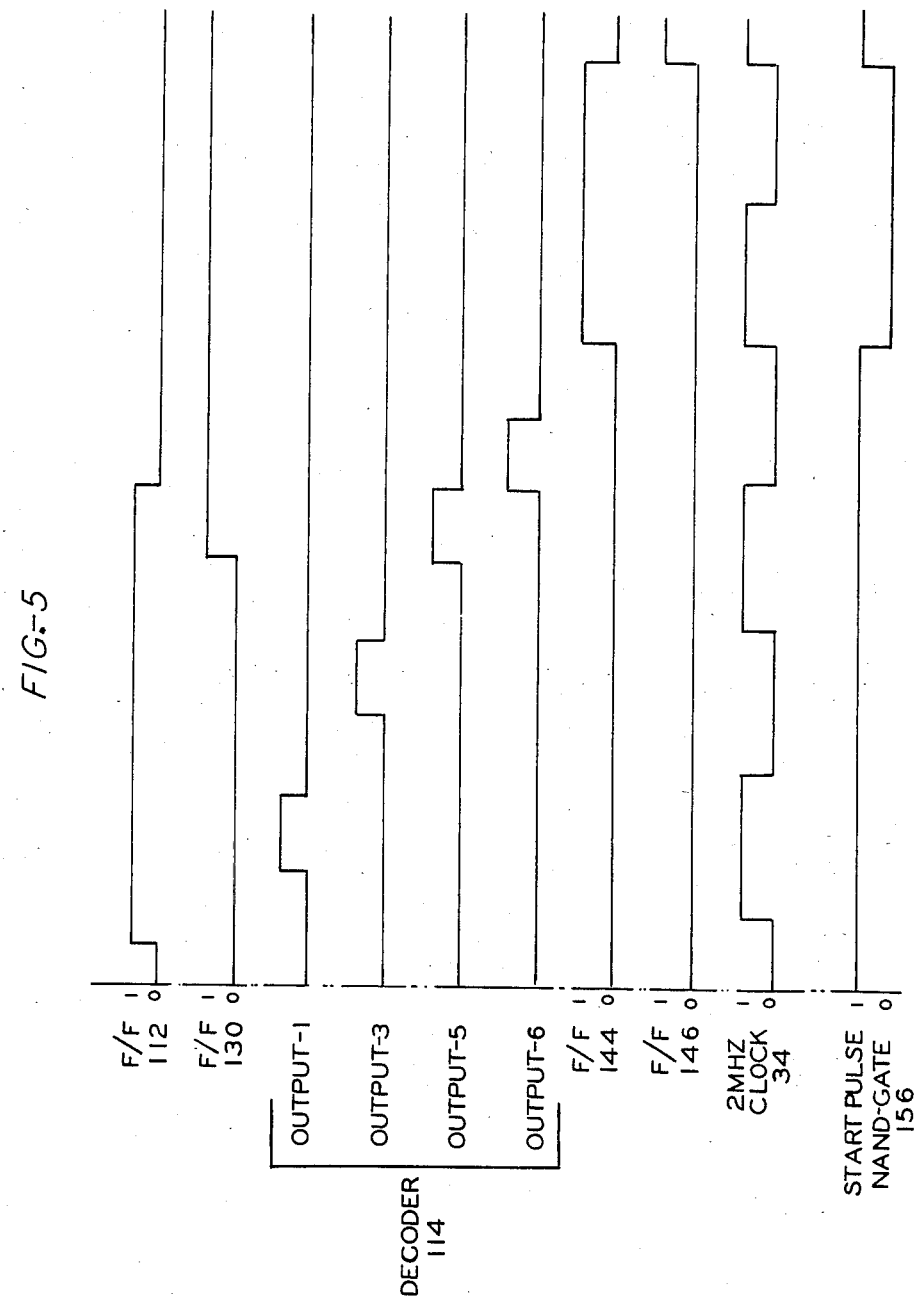

SCANNING SAMPLE, SIGNAL GENERATION, DATA DIGITIZING AND RETIMING SYSTEM

TECHNICAL FIELD

This invention relates to the handling of video signals and more particularly to the generation of a video scanning timing signal, sampling a video signal to determine the pattern of presence or absence of a condition on the surface of a substrate and retiming the video signal for later efficient logical analysis.

BACKGROUND OF THE INVENTION

Generally, to automatically inspect a printed wiring board pattern, U.S. Pat. No. 4,152,723 granted to D. H. McMahon et al., on May 1, 1979, discloses using a helium-cadmium, blue laser beam that is swept by a rotating mirror across a portion of the printed wiring board surface. The copper conductors of the printed wiring board reflect the blue light, but the insulating substrate surface fluoresces orange in response to the blue laser beam. The light reflected from or fluoresced by the printed wiring board passes through a blue-blocking filter onto a photomultiplier tube. The output of the photomultiplier tube is then detected as a binary representation pattern of the presence or absence of copper along the line of spots over which the laser beam sweeps, thereby eventually generating an accurate representation of the printed wiring board's surface.

U.S. Pat. No. 4,185,298 granted to Billet et al., on Jan. 22, 1980, discloses the automated inspection of patterns such as a printed circuit board by scanning the test board and a master or standard board known to be accurate. The scanning is done with a pair of TV cameras, the outputs of the cameras are compared, and an error signal is produced when the outputs do not coincide.

U.S. Pat. No. 4,338,626 granted to J. H. Lemelson on July 6, 1982, discloses a system for comparing a video signal with a reference or standard signal that is recorded on magnetic tape or on a magnetic drum.

U.S. Pat. No. 3,835,249 granted on Sept. 10, 1974, to A. J. Dattilo et al., discloses a system for indicating the precise position of a scanning light beam (scanned by a rotating multifaceted mirror). The scanning light beam is split into two paths by a beam splitter. The two paths comprise a utilization path and a synchronization path. The portion of the light beam traversing the synchronization path scans an optical grating. The light passing through the grating is detected to provide an output signal which can be used to indicate the position of the scanning beam traversing the utilization path. In this way, a binary signal can be used with subsequent electronics, such as a binary counter, to identify or control a video signal at actually known positions along the sweep of the beam.

As the above references illustrate, in the manufacture of printed wiring boards, it is desired to inspect the printed wiring pattern on the board in order to discover and possibly correct any defects in the copper pattern which might cause operational difficulties in the finished printed circuit. Typically, these defects comprise nicks in the edges of a copper path which may actually cause a break in the circuit, or enlargement of the copper path so as to diminish the spacing between adjacent copper conductors sufficiently to cause bridging and resultant conduction between the paths. With the ever-increasing size of printed wiring boards and the decreasing conductor size and spacing, manual inspection of a printed wiring board approaches a practical impossibility.

As disclosed in the above-mentioned McMahon patent when a beam of blue laser light energy strikes a treated fiberglass-epoxy substrate, the substrate fluoresces orange. The orange light is then filtered to remove any blue component and is passed to one or more photomultiplier tubes in order differentially to sense the copper covered areas of the printed wiring board and distinguish them from the exposed areas of the substrate. As disclosed in the McMahon reference, the beam of laser light is preferably swept across a portion of the printed wiring board by means of a rotating mirror. Typically, such swept systems, which have been known since before the invention of the laser, usually produce the resultant data in short bursts punctuated by long pauses between bursts of data.

It is rare that the sweep across a reasonable length of a printed wiring board can be accomplished at a uniform speed. Consequently, typically, the speed of sweep varies from one end of the sweep to the center of the sweep to the opposite end of the sweep. However, it is important to sample the data at uniform length spacings of the swept beam. This is to avoid distortion of the electronic representation of the surface being swept.

An important factor in the inspection of a printed wiring board is the uniformity of width of the copper conductors. If the electronic representation shows a conductor wider at the end of the beam's sweep than another conductor at the center of the beam's sweep, an error signal might result. Conversely, an improperly sized conductor could pass inspection merely by reason of its location within the length of the sweep.

SUMMARY OF THE INVENTION

In accordance with one aspect of the present invention, the instantaneous magnitude of a binary video signal is stored so as to produce a decaying representation of the magnitude of that signal. In response to the decaying representation of a magnitude of the video signal, the sensitivity of the sensor is adjusted in order to maintain a constant peak instantaneous magnitude of the measured signal. A binary decision criterion is established at an arbitrary proportion of a decaying representation of the stored peak sensed video signal.

In another aspect of the present invention, binary video signals are stored at the high frequency at which they are generated and then read out at a slower rate in order to extend each binary signal and improve the duty cycle of the video signal to approach one hundred percent. The slowing of the video signals is accomplished by routing alternate bursts of the high speed video signal to alternate memory devices while simultaneously reading out at the slower speed from the other memory device.

Still another aspect of the present invention, involving a beam splitter and timing pulse generation system using an optical grating, an oscillating system is used in the timing signal path which oscillating system is tuned to the approximate frequency of the timing signals, so as to produce or fill in a timing signal should a timing signal be missing from the stream generated by the optical grating.

In still yet another aspect of the present invention, a frequency doubler is provided in order to permit the use of a less dense optical grating in order to minimize the likelihood of loss of timing signals due to damage to the grating or to an accumulation over time of contamination on the grating.

BRIEF DESCRIPTION OF THE DRAWINGS

FIG. 4 is a timing diagram representing an entire sweep interval of the system of FIGS. 1-3; and FIG. 5 is an expanded timing diagram of the first portion of the timing diagram illustrated in FIG. 4.

DETAILED DESCRIPTION

Figure 1:
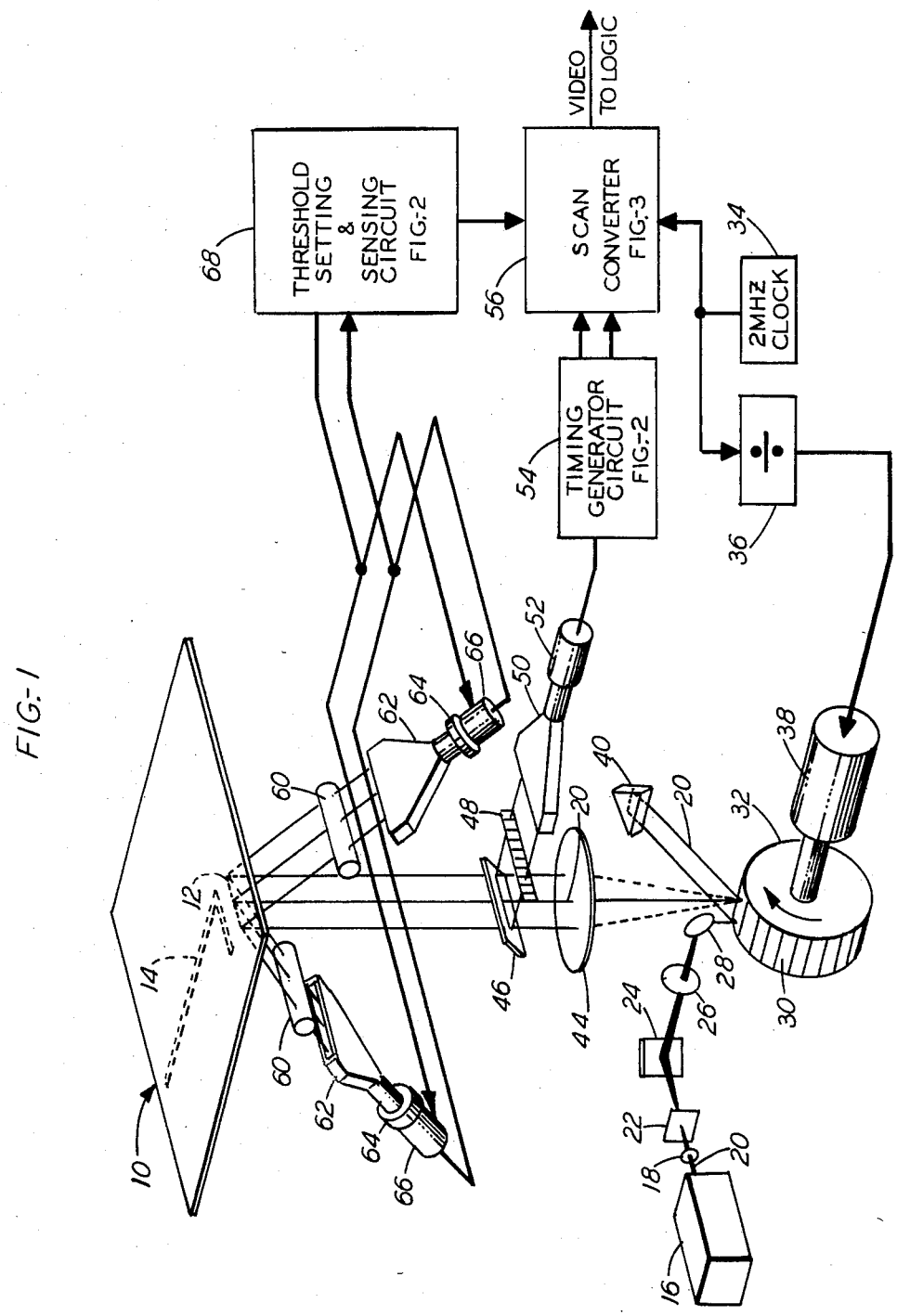
FIG. 1 is an overall outline of the optical scanning system utilizing the present invention.

Referring now to FIG. 1, a printed wiring board 10 is shown in the test position at which a spot of light formed by a laser beam can sweep a short path across a field 12 on its underside, where the printed-wiring pattern composed of at least one copper conductor 14 is located. The length of the path 12 is determined by the optical characteristics of the sweeping system. In a preferred system, the printed wiring board 10 moves in a direction perpendicular to the path 12 in increments equal to the diameter of the spot (preferably 0.001-inch in diameter), thereby sweeping a raster or pattern, the width of the raster pattern being equal to the length of the path 12. The length of each raster pattern can extend as far as it is desired to move the board 10 in increments perpendicular to the path 12. In order to examine an entire board 10, successive raster patterns are swept adjacent to one another, so as to blanket the surface of the board. Therefore, after each raster pattern has been swept, the printed wiring board 10 is indexed in a direction parallel with the path 12, in order to sweep an adjacent raster pattern on the board surface.

The optical energy that is swept across the board 10 is generated by a conventional helium-cadmium laser 16. The output of the laser comprises a blue laser beam 20 that passes through a first lens 18 which reduces the diameter of the beam. The laser beam 20 then passes through a pinhole filter 22, in order to remove fringing radiation and confine the beam to a very small diameter with clean, sharp edges. The laser beam 20 is reflected by a mirror 24, passes through a collimating lens 26, and is reflected by another mirror 28 onto one of the facets 30 of a rotating mirror drum 32.

A two MHz crystal clock 34 generates accurately-timed clock pulses that are divided in a divider 36, such as a binary counter, and delivered to a synchronous motor 38. The motor 38 drives the rotating mirror drum 32 at a very accurately-controlled rotational speed.

The laser beam 20, reflected from a mirror facet 30, enters a prism 40 and is reflected back out of the prism onto the same mirror facet 30 on the surface of the mirror drum 32. The laser beam 20, as reflected the second time from the facet 30, possesses the desired degree and speed of sweep. The frequency of the clock 34, the divisor of the divider 36 (determined by the number of binary stages of the binary counter), coupled with the number of poles of the motor 38 and the number of facets 30 on the drum 32 determines the nominal sweep speed of the laser beam.

The sweeping laser beam 20 then passes through an objective lens 44 having a focal length and position calculated to bend the sweeping laser beam 20 from a series of angled paths, illustrated in FIG. 1 by dotted lines extending from the facet 30 to the objective lens, into a series of parallel paths. Those parallel paths are perpendicular to the printed wiring board 10 at any point in the sweep of that beam and are illustrated in FIG. 1 by the three parallel lines extending from the objective lens 44 to the path 12 on the printed wiring board 10 that preferrably illuminates a spot on the board 10 that is 0.001-inch in diameter.

The sweeping beam, as it now sweeps in a series of parallel paths after passing through the objective lens 44, strikes a 3% beam splitter 46. The beam splitter 46 passes 97% of the energy of the laser beam 20 to the surface of the printed wiring board 10 but reflects 3% of the laser beam's energy to a graticule or optical grating 48. The optical grating 48 is placed so that it is also illuminated by a spot of the laser light that is preferrably 0.001-inch in diameter. As the 3% of the laser beam 20 is swept across the optical grating 48, the 3% of the laser beam is alternately blocked or passed by the alternately clear and opaque lines of the optical grating. The laser light that passes the optical grating 48 is collected by a fiber-optic bundle 50 which conveys this optical energy to a photomultiplier tube 52. The output of the photomultiplier tube 52 is delivered as a timing signal to a timing generator circuit 54 which will be explained in greater detail in conjunction with FIG. 2.

The remaining 97% of the laser beam 20 that strikes the printed wiring board 20 along the path 12, is simply reflected and diffused by the copper foil of the conductor paths or is partly reflected by the treated surface of the fiberglass-epoxy substrate, of which the bulk of the printed wiring board 10 is constructed. The surface of the epoxy-glass substrate of the printed wiring board 10 is preferably treated in order to fluoresce orange upon being illuminated with a helium-cadmium laser beam. Therefore, when the laser beam 20 strikes the copper foil on the surface of the printed wiring board 10, only reflected blue light is available. However, when the laser beam 20 strikes a portion of the treated surface of the fiberglass-epoxy substrate of the printed wiring board 10, that portion of the surface fluoresces orange so there is then orange and blue light available to be detected.

While copper conductors have been mentioned as being present on an insulating fluorescent substrate, the nature of surface of the product inspected can be any combination that will result in a difference from an optical scan. Another example of a product surface to be inspected is a copper foil selectively coated with a fluorescent etch-resistant material in a negative pattern of the desired pattern of copper conductors.

The fluorescent orange and the blue light that is available at the surface of the printed wiring board 10 is collected by a pair of cylindrical lenses 60, each of which focuses the collected light energy onto the ends of the fiber-optic strands of a fiber-optic bundle 62, which may be identical to the fiberoptic bundle 50. The two fiber-optic bundles 62 carry the light energy to a pair of associated blueblocking filters 64, which block the blue laser light and let only the orange fluorescent light pass to a pair of photomultiplier tubes 66. The photomultiplier tubes 66 generate an output each time that they are energized by orange light fluorescing from a portion of the printed wiring board 10 that is not covered with copper foil. The outputs from the two photomultiplier tubes 66 are combined and delivered to a threshold setting and sensing circuit 68.

Figure 2:
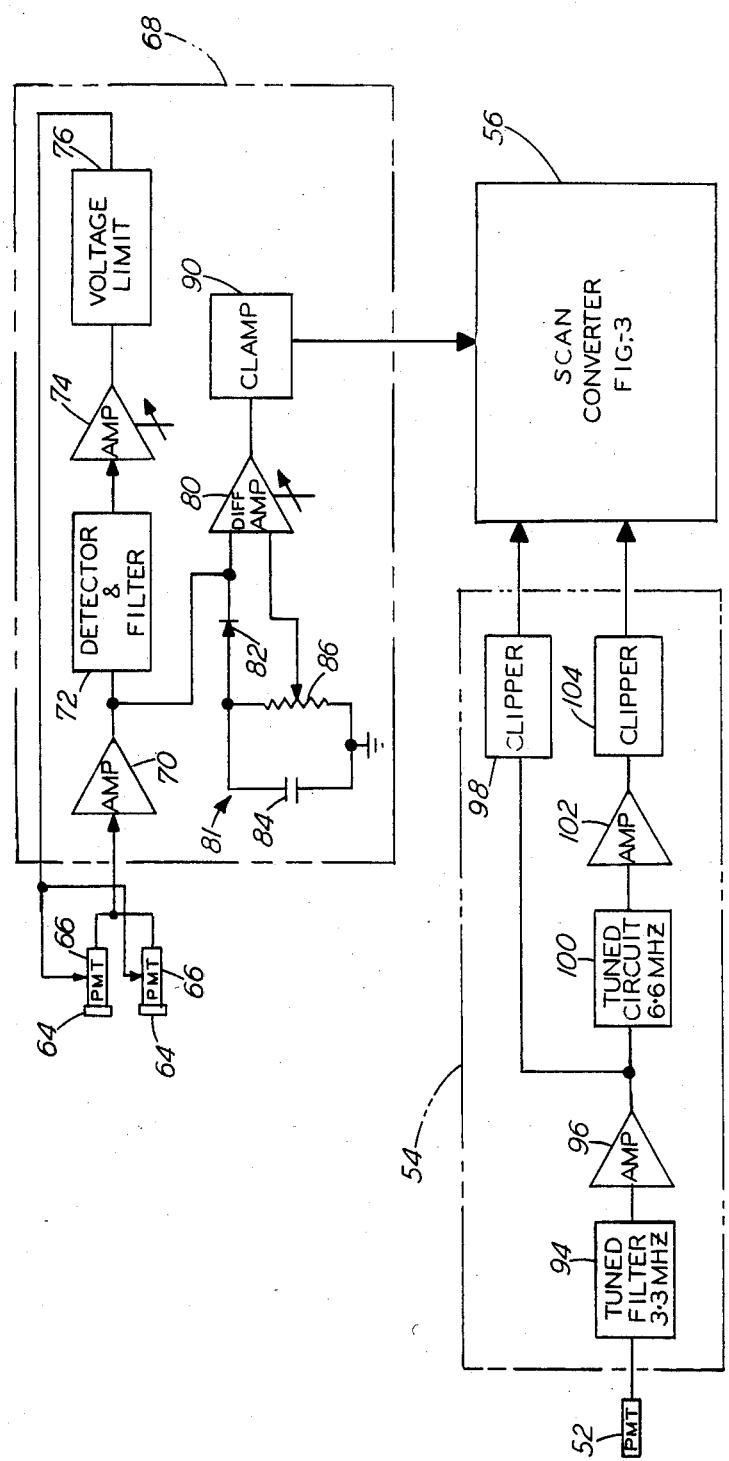
FIG. 2 shows the threshold setting and sensing circuit of FIG. 1, in block diagram form and also the frequency doubler circuit and tuned signal restoration circuit for producing the sweep-location-dependent timing signals.

Referring now to FIG. 2, the threshold setting and sensing circuit represented by the block 68 and the timing generator circuit 54 in FIG. 1 are shown in greater detail. The video signals representing the presence or absence of a copper conductor 14 on the printed wiring board 10 is received from the photomultiplier tubes 66 are combined and amplified by an amplifier 70. The output of the amplifier 70 is delivered to a detector and filter circuit 72. The detector and filter circuit 72 contains a diode, a capacitor, and a bleed resistor similar to the audio detector circuit in any AM radio. Therefore, the RC time constant of the detector is adjusted to be long with respect to the characteristic frequency (preferrably, about 6.6 MHz) of the video signals received from the photomultiplier tubes 66.

The output of the detector and filter circuit 72 is a decaying voltage representative of the peak signal amplitudes received by the amplifier 70. That decaying representation is boosted and renewed each time that a peak signal is received by the amplifier 70—as when the laster beam 20 illuminates a spot of the fluorescent substrate and fluorescent orange light is produced.

The output of the filter circuit 72 is delivered to an adjustable amplifier 74 which can be adjusted manually to control the signal amplitude received from the photomultiplier tubes 66.

It is an operating characteristic of a photomultiplier tube that its gain or the voltage of its output signal is a function of its bias voltage. Therefore, in order to increase the voltage output for any given optical input, the bias voltage of the photomultiplier tube is increased. Conversely, to reduce the output voltage resulting from an input of optical energy, the bias of the photomultiplier tube is reduced. The detector and filter 72, in conjunction with the amplifier 74, comprises a feedback loop to produce a constant level of peak output voltage from the photomultiplier tubes 66 over a moderately large range of optical energy inputs. The detector and filter 72 serves to provide a feedback voltage of the signal output resulting from the receipt of an orange fluorescent optical signal, to maintain a constant level of voltage representative of an orange signal. The adjustable amplifier 74, in the feedback loop depicted in FIG. 2, allows manual adjustment of that voltage for an orange signal.

The output from the amplifier 70 is an analog voltage signal. The very low voltages represent the light reflected when the laser beam 20 strikes non-fluorescent portions (e.g., copper) of the surface of the printed wiring board 10. The higher voltages represent the orange fluorescent light that results when the laser beam 20 strikes exposed portions of the surface of the substrate of the printed wiring board 10.

Besides being delivered to the detector and filter 72, the output of the amplifier 70 is also delivered to one input of a differential amplifier 80 and to another detector circuit 81 comprising a diode 82, a capacitor 84, and a potentiometer 86. The detector circuit 81 has a time constant that is long with respect to the video output signal from the photomultiplier tubes 66 but is short with respect to the time constant of the RC filter within the detector and filter circuit 72. The purpose of the detector circuit 81 is to provide a decaying reference voltage characteristic or representative of the peak signal voltages that represent the orange light from the exposed substrate of the printed wiring board 10. The tap of the potentiometer 86 is then used to provide one input to the amplifier 80 which is a fixed percentage of the voltage representative of that orange light amplitude. The output of the differential amplifier 80 is then a binary voltage, one voltage level representative of only blue light that results from reflection of the laser beam 20 from a copper conductor 14 and the other voltage level representative of orange light generated at the uncovered surface of the fiberglass-epoxy substrate of the printed wiring board 10. The output of the amplifier 80 is delivered to a clamping circuit 90 in order to prevent excessive voltage being applied to subsequent circuit components. The output of the clamp 90 constitutes the output of the threshold setting and sensing circuit 68 and is a binary video data output signal delivered to the scanning converter circuit 56 of FIG. 1, which is explained in greater detail in conjunction with FIG. 3.

FIG. 2 also shows in greater detail the timing generator circuit 54 which receives the output from the photomultiplier tube 52 of FIG. 1. The output from the photomultiplier tube 52 results from the passage of 3% of the energy of the laser beam 20 through the optical grating 48 and is approximately a sinusoid of 3.3 MHz.

However, the use of the optical grating 48 (FIG. 1) to generate the input to the timing generator circuit 54 means that the approximate sinusoidal signals from the photomultiplier tube 52 are actually pulses of signal energy representative of the presence of the spot of the laser beam 20 at particular locations along the path 12. These pulses of signal energy from the photomultiplier tube 52 occur only nominally at 3.3 MHz. They actually vary in frequency with the varying sweep speed of the laser beam 20 as it sweeps the path 12.

This signal from the photomultiplier tube 52 is delivered to a tuned filter 94. The filter 94 is tuned to 3.3 MHz, the approximate or nominal frequency of the signals received from the photomultiplier tube 52. The signals that pass through the filter 94 are delivered to an amplifier 96, which delivers the filtered and amplified sinusoidal signals to a clipper 98. The filter 94, while tuned to the nominal frequency of the expected signals from the photomultiplier tube 52, has a "Q" that is sufficiently low to pass the range of frequencies anticipated for the signals from the photomultiplier tube. The clipper 98 receives the fairly high voltage sinusoidal signals at a nominal 3.3 MHz from the amplifier 96 and clips the vast majority of the signals to produce essentially a square wave at the actual frequency of the signals received from the photomultiplier tube 52. This square wave at a nominal 3.3 MHz represents the actual, physical movement of the spot of the laser beam 20 as it sweeps the path 12 and is delivered to the scan converter 56 of FIG. 3 principally for use in starting a cycle of operation of the scan converter of FIGS. 1 and 3, as will be explained in greater detail.

The output of the amplifier 96 is also delivered to a tuned circuit 100, which is tuned to oscillate at 6.6 MHz, twice the frequency of the tuned filter 94. The tuned circuit 100 delivers its output signal to an amplifier 102, which in turn drives a clipper 104 to provide a square wave output which is nominally at 6.6 MHz, twice the 3.3 MHz nominal frequency of the square wave output from the clipper 98. The output of the clipper 104 is delivered to the scan converter circuit 56 of FIGS. 1 and 3 and is used principally to control the sampling of the binary video signal delivered to the scan converter 56 by the threshold setting and sensing circuit 68 of FIGS. 1 and 2.

By using the tuned circuit 100 to double the frequency of the timing signals generated ultimately by the optical grating 48, the optical grating can have coarser grating lines and thus can be less prone to obstruction by contamination. The tuned circuit has sufficient "Q" to "ring" a bit. That is, the tuned circuit 100 will continue to oscillate for several cycles after receiving an energizing input. Therefore, if one or two timing pulses are missing (by reason of contamination, of the optical grating 48 for example), the tuned circuit 100 will "ring" through those missing timing pulses and continue to generate sampling-control pulses for the binary video signal. Consequently, no data will be lost or improperly recorder.

Figure 3:
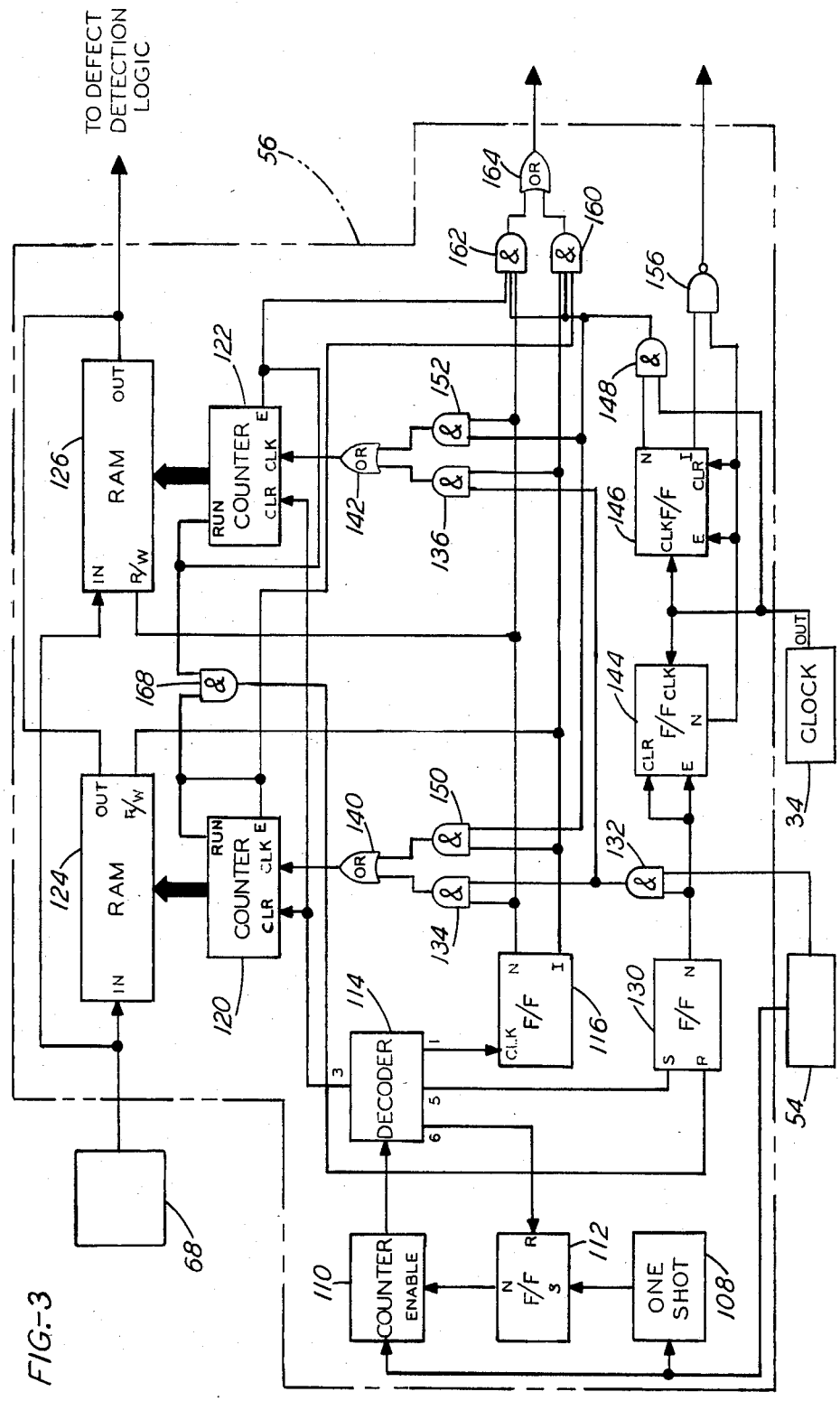
FIG. 3 shows the scan converter used to reduce the speed or frequency of video signals and thus to increase the duty cycle of the video signal.

Referring now to FIG. 3, the scan converter 56 is shown in greater detail. The threshold setting and sensing circuit 68 is illustrated to show its relationship to the internal circuitry of the scan converter 56. The filter and doubler circuit 54 and the 2-MHz clock 34 are also shown in FIG. 3 to enhance the explanation of the scan converter 56.

FIG. 4 illustrates the approximate timing of the scan converter 56 through one basic cycle of operation. FIG. 5 illustrates the timing of the first portion of a cycle of operation of the scan converter 56 in order to illustrate the start-up of a cycle.

As the 3% of the laser beam 20 begins a scan of the optical grating 48, the first pulse of the signals generated by the photomultiplier tube 52 passes through the filter and doubler circuit 54, and the first 3.3 MHz pulse is delivered from the clipper 98 (FIG. 2), to a monostable multivibrator or one-shot 108 (FIG. 3) and also to a binary counter 110. This is the leftmost full pulse in the waveform labeled "PMT 52" of FIG. 4. The one shot 108 is set from its stable state to its quasistable state by the first timing pulse that is generated when the laser beam 20 is at a position such that its 3% portion strikes the first clear area of the optical grating 48, and energizes the photomultiplier tube 52. The output from the one shot 108, when the one shot is set to its quasistable state, sets a bistable multivibrator or flip-flop 112 to its binary "1" state at which its normal or "N" output delivers a "1" signal. The flip-flop 112 starts a cycle in its "0" state as illustrated in the waveform labeled F/F 112 in FIG. 5. The normal output of the flip-flop 112 energizes the enable input of the counter 110.

Because of time delays inherent in the setting of the one-shot 108, the flip-flop 112, and the enabling of the counter 110, the counter 110 does not count that first timing pulse that had set the one-shot 108. However, as long as flip-flop 112 remains in its "1" state, the counter 110 will count succeeding timing pulses. Succeeding timing pulses from the clipper 98 of the timing generator circuit 54 increment the counter 110.

The output of the counter 110 is delivered to a decoder 114 which decodes the counter's output and, in response to selected counts, generates signals in a predetermined sequence. The simplest configuration for the decoder 114 is a series of AND-gates or NOR-gates.

The first output from the decoder 114 triggers a bistable multivibrator or flip-flop 116, causing that flip-flop to change its binary state from "0" to "1" or from "1" to "0". The flip-flop 116 is thus triggered only once for each sweep of the laser beam 20. Therefore, the flip-flop 116 can identify alternate sweeps of the laser beam 20.

Chronologically, the third count decoded by the decoder 114 in response to the fourth clear area of the optical grating 48, causes the decoder 114 to issue an output which is delivered to the "clear" input of two eleven-stage, 2048-count binary counters 120 and 122. Such a clear signal resets the binary counters 120 and 122 to their initial or zero-count condition. When the counters 120 and 122 are reset, their "RUN" outputs deliver enable signals to their own enable or "E" inputs to enable the counters to respond to subsequent clock or timing signals at their clock or "CLK" inputs.

The outputs of the binary counters 120 and 122 form the address inputs to an associated pair of random access memories 124 and 126. The random access memories 124 and 126 are bit addressed rather than byte addressed, in that a single address count addresses only a single bit location within the random access memory. The data stream that comprises the binary video output from the threshold setting and sensing circuit 68 is delivered to the data input terminals of both random access memories 124 and 126. The normal or "N" output from the flip-flop 116 is connected to the read/write input of the random access memory 126. The inverted or "I" output of the flip-flop 116 is connected to the read/write input of the random access memory 124. The random access memories 124 and 126 are arranged to record input data when their read/write inputs receive binary "0" signals. Therefore, when the flip-flop 116 is in its "0" state, its normal output energizes the read/write input of the random access memory 126, causing that random access memory to record seriatim burst of the video data received at a nominal 6.6 MHz from the threshold setting and sensing circuit 68. While the random access memory 126 is recording, the random access memory 124 is reading its contents out seriatim at its output terminal, at a reduced bit rate or speed, to a logic system (not shown) for further analysis.

When the flip-flop 116 is in its "1" state, its inverse output, which then issues a binary "0" signal, energizes the read/write input of the random access memory 124, causing it to record seriatim the video output from the threshold setting and sensing circuit 68. Simultaneously, the random access memory 126 is in the output or read mode in which its output terminal delivers signals seriatim to analysis logic (not shown) at a lower bit rate or baud.

Returning to the decoder 114, at the sixth signal generated by the 3% of the laser beam 20 that passes through openings in the optical grating 48, the decoder 114 produces an output pulse at its "5" output, which is a set signal sent to the set input of a flip-flop 130 to set that flip-flop to its "1" state. The normal output of the flip-flop 130 provides one of the inputs to an AND-gate 132. The other input to the AND-gate 132 is derived from the double-frequency output of the filter and doubler circuit 54. Therefore, when the flip-flop 130 is set to its "1" state, the double-frequency (6.6 MHz) timing pulses are issued from the AND-gate 132 to a pair of AND-gates 134 and 136.

The timing pulses that issue from the AND-gate 132 represent movements of the sweep of the laser beam 20 equal to the diameter of the laser beam as it impinges on the surface of the printed wiring board 10. Therefore, the AND-gate 132 issues one timing pulse for each physical location on the printed wiring board 10 that is swept by the laser beam 20. The other input of each AND-gate 134 and 136 is connected to the normal and inverted output, respectively, of the flip-flop 116.

Therefore, the AND-gates 134 and 136 are alternately energized to pass the timing pulses from the AND-gate 132. The AND-gates 134 and 136 are energized on alternate sweeps of the laser beam 20.

If the flip-flop 116 is in the binary "1" state, the output of the AND-gate 134 passes through an OR-gate 140 to the clock input of the counter 120. Therefore, the counter 120 advances one count for each location across the sweep of the laser beam 20. Consequently, as the laser beam 20 sweeps across an area of the printed wiring board 10, the counter 120 addresses successive memory locations within the memory 124. This causes the binary state of the output of the threshold setting and sensing circuit 68 to be stored at those successive memory locations in the random access memory 124, in order to store in that random access memory the binary indication of whether or not a copper conductor 14 existed at each spot on the printed wiring board 10 as the laser beam 20 swept across the printed wiring board. While the flip-flop 116 is in the binary "1" state, the AND-gate 136 is disabled, and the random access memory 126 is in the read mode and, as will be explained below reads out the data from the previous sweep of the laser beam 20.

If the flip-flop 116 is in its binary "0" state, the random access memory 126, rather than the random access memory 124, is placed in the write mode. The AND-gate 136 is then energized, and the timing pulses from the AND-gate 132 pass through the AND-gate 136 and through an OR-gate 142 to the clock input of the counter 122, which then addresses successive locations of the random access memory 126. Meanwhile, the random access memory 124 reads out the data from the previous sweep of the laser beam 20.

The 6.6 MHz timing pulses that pass through the AND-gate 132 are indicative of the sweep of the laser beam 20, and are at a higher frequency than the 2 MHz clock rate of the analysis logic (not shown) that is expected to analyze the video data in order to find flaws in the surface of the printed wiring board 10.

Typically, a video signal issues from the threshold setting and sensing circuit 68 during only about 30% of the total cycle time of the machine. This is referred to as a 30% duty cycle. During this brief period of high speed pulses, the video signal from the threshold setting and sensing circuit 68 fills with 2048 bits of video data whichever of the random access memories 124 or 126 happens to be in the write mode. However, that total amount of information, 2048 bits, is read out of the random access memory 124 or 126, whichever is in the read mode, at less than ⅓ of the frequency of the write mode.

To control the read mode of the random access memories 124 and 126, the output of the flip-flop 130 is also delivered to both the clear input and the enable input of a flip-flop 144, which assures that the flip-flop 144 is in its "0" state and enables that flip-flop to respond to the next clock pulse from the 2 MHz clock 34 (FIG. 5). The next clock pulse from the output of the clock 34 is delivered to the clock input of the flip-flop 144 and sets that flip-flop to its "1" state.

The normal output of the flip-flop 144 is connected to the enable and clear (or reset) inputs of a flip-flop 146. Therefore, when the flip-flop 144 assumes its "1" state, it assures that the flip-flop 146 is in its "0" state and enables the clock input of the flip-flop 146. Consequently, the next output pulse from the clock 34 that follows the clear or reset of the flip-flop 146 sets the flip-flop 146 to its "1" state. When the flip-flop 146 assumes its "1" state, it normal output, which is connected to an AND-gate 148, enables that AND-gate.

After the AND-gate 148 receives a "1" input from the flip-flop 146, successive clock pulses from the output of the clock 34 pass through the AND-gate 148 and are delivered to a pair of AND-gates 150 and 152. It will be noted that the other inputs of the AND-gates 150 and 152 are connected to the inverted and normal inputs, respectively of the flip-flop 116.

Therefore, when the AND-gate 134 is enabled to pass the 6.6 MHz timing pulses from the AND-gate 132, the AND-gate 150 is disabled. Similarly, when the AND-gate 152 is enabled to pass clock pulses from the clock 34 and the AND-gate 148, the AND-gate 136 is disabled. When the flip-flop 116 is in its "0" condition, the AND-gate 150 is enabled, the AND-gate 134 is disabled, the AND-gate 136 is enabled, and the AND-gate 152 is disabled. In this way, the flip-flop 116 controls the routing of 6.6 MHz timing pulses from the AND-gate 132 to one of the counters 120 or 122, while simultaneously routing the 2 MHz clock pulses from the clock 34 to the other of the counters 122 or 120. Therefore, the random access memories 124 and 126 are alternately filled with the video signal from the threshold setting and sensing circuit 68 at the rate of the 6.6 MHz pulses passing through the AND-gate 132 or are issuing stored video data signals from the prior sweep of the laser beam 20 at the 2 MHz clock rate of the clock 34.

Referring again to the decoder 114 of FIG. 3 and FIG. 5, output 6 of the decoder is connected to the reset input of the flip-flop 112. Therefore, the sixth count of the counter 110 resets the flip-flop 112 to its "0" condition, disabling the counter until the beginning of the next sweep of the laser beam 20.

It is desired to send a start-of-line pulse to the subsequent defect-detection logic (not shown) when the flip-flop 144 is in its "1" state but before the flip-flop 146 assumes its "1" condition and is still in its "0" state. Therefore, the normal output of the flip-flop 144 and the inverse output of the flip-flop 146 are connected to the inputs of a NAND-gate 156. Referring to FIG. 5, the output of the NAND-gate 156 is normally in the "1" state. However, when the normal output of the flip-flop 144 and the inverted output of the flip-flop 146 are both "1", the output of the NAND-gate 156 is a "0" state pulse. This "0" pulse at the output of the NAND-gate 156 is a start pulse to enable the defect-detection logic (not shown) to begin receiving a line of data pulses from whichever random access memory 124 or 126 is in the read mode.

The defect-detection logic operates from the same 2 MHz clock 34 as the random access memory 124 or 126 that is in the read mode. To assure that the defect-detection logic gets clock pulses only when data are available from the random access memories 124 or 126, the run outputs of the counters 120 and 122 are also connected to one input, each, of two AND-gates 160 and 162, respectively. Any other input of each AND-gate 160 and 162 is connected to the inverted and normal output, respectively of the flip-flop 116. The third input to each of the two AND-gates 160 and 162 is supplied by the AND-gate 148 which passes the 2 MHz clock signals. Therefore, while whichever random access memory 124 or 126 that is in the read mode is receiving 2 MHz clock signals, an AND-gate 160 or 162 is passing those same 2 MHz clock signals. The outputs of the AND-gates 160 and 162 pass through an OR-gate 164 to the defect-detection logic (not shown).

When each of the counters 120 and 122 reaches its maximum count of 2048 its RUN output changes state and removes its enable or "E" input. Therefore, counting ceases at that counter. Whichever counter 120 or 122 is receiving 6.6 MHz timing pulses from the AN-gate 132 will be the first to reach its maximum count. However, the other counter 122 or 120 must continue counting the 2 MHz clock pulses until it has reached its complete count of 2048. When the slower counter reaches that 2048 count, it, too, changes the state of its RUN output. The RUN outputs of the two counters 120 and 122 are connected as the two inputs of an AND-gate 168. When both counters 120 and 122 have changed their RUN outputs and stopped, the AND-gate 168 sends a reset signal to the reset input of the flip-flop 130. The reset of the flip-flop 130 to its "0" state disables the AND-gate 132 and prevents that AND-gate from passing any further 6.6 MHz timing pulses.

During the idle time of the laser beam 20, when the faster of the two counters 120 and 122 has stopped the random access memory 124 or 126 that is in the read mode continues to deliver data to the defect-detection logic (not shown) at the lower frequency of the 2 MHz clock 34, and the 2 MHz clock pulses continue to pass through one of the AND-gates 160 or 162 and the OR-gate 164 to the defect-detection logic. When the slower counter 120 or 122 a count of 2048, its RUN output changes state and stops that counter. The RUN output of the slower counter 120 or 122, when that counter stops, also removes an enable input from the one of the two AND-gates 160 or 162 that had been passing 2 MHz clock pulses to the defect-detection logic. That stops the flow of 2 MHz clock pulses to that defect-detection logic.

The 2 MHz clock also indirectly controls the frequency of the 6.6 MHz timing pulse signals. The motor 38 (FIG. 1) that drives the rotating mirror drum 32 is synchronized with the read-out of data at a 2 MHz rate from the random access memories 124 and 126 (FIG. 3) by way of the clock 34 (FIGS. 1 & 3) and the frequency divider 36 (FIG. 1). Therefore, the rotation of the mirror drum 32 can be very closely controlled so that the next sweep of the laser out of the random access memory 124 or 126.

What is claimed is:

1. A system for generating timing signals in spaced synchronism with the movement of a laser beam comprising:
    means for sweeping the laser beam across a swept space;
    means for dividing the sweeping laser beam into a major portion and a minor portion, the major portion swept across the swept space;
    an optical grating positioned in the path swept by the minor portion;
    a photosensor for generating timing signals from the portion of the laser beam that passes through the optical grating;
    a filter for blocking components of the timing signals that are in a frequency band outside of a predetermined frequency range;
    a circuit tuned to oscillate at twice the frequency of the predetermined frequency range, said circuit receiving the signals that pass through the filter, the tuned circuit having sufficient ringing capability to continue oscillating with substantial energy for a plurality of cycles absent signals passing through the filter.

2. A data stream speed-reduction and duty-cycle-improvement system comprising:
    a first random access memory having address inputs;
    a data input and a data output;
    a first binary counter, in the first mode counting timing signals and in the second mode counting clock pulses, having outputs connected to the address inputs of the first random access memory;
    a second random access memory having address inputs;
    a data input and a data output;
    a second binary counter, in the first mode counting clock signals and in the second mode counting timing signals, having outputs connected to the address inputs of the second random access memory;
    means for generating timing signals at the first, higher frequency;
    clock means for generating clock signals at the second, lower frequency;
    a bistable circuit, stable in either a "1" state or a "0" state, having facility for changing state when alternation is required;
    a first plurality of steering gates, enabled when the bistable circuit is in the "1" state for conveying timing signals from the timing signal generating means to the first counter and clock signals from the clock signal generating means to the second counter; and
    a second plurality of steering gates, enabled when the bistable circuit is in the "0" state for conveying timing signals from the timing signal generating means to the second counter and clock signals from the clock signal generating means to the first counter.

3. A system according to claim 14 further comprising means responsive to the first plurality of a group of timing signals for changing the state of the bistable circuit.

4. A data stream speed-reduction and duty-cycle-improvement system comprising:
    first memory means for selectively storing data of the data stream at a first, higher frequency and for reading said data out at a second, lower frequency;
    second memory means for selectively storing data of the data stream at a first, higher frequency and for reading said data out at a second, lower frequency;
    means for alternating between a first mode and a second mode, in the first mode for causing the first memory means to store data while causing the second memory means to read out data, in the second mode for causing the second memory means to store data while causing the first memory means to read out data;
    means for generating timing signals at the first, higher frequency;
    clock means for generating clock signals at the second, lower frequency; and
    means responsive to the clock signal generating means for controlling the frequency of the timing signals generated by the timing signal generating means.

5. A system according to claim 16 wherein the controlling means comprises:

means responsive to the output of the clock signal generating means for generating drive signals at a frequency that is a fraction of the frequency of the clock signals;

a synchronous motor driven by the drive signal generating means at a speed which is in synchronism with the clock signals;

a source of focused energy;

means driven by the motor for modulating the focused energy in synchronism with the clock signals; and means for sensing the modulated energy and for controlling the operation of the timing signal generating means in response to the frequency at which the focused energy is modulated.

6. A system according to claim 17 wherein the modulating means comprises:

a drum connected for rotation with the motor, the drum being positioned to intercept at its periphery, the focused energy;

a plurality of mirrors on the periphery of the drum, positioned to reflect the focused energy, whereby rotation of the mirrored drum sweeps the reflected, focused energy in a path; and means located in the path swept by the focused energy for alternately blocking and passing the focused energy to the sensing means.

7. A data stream speed-reduction and duty-cycle improvement system comprising:

a first memory for receiving, storing, and transmitting data seriatim;

a second memory for receiving, storing, and transmitting data seriatim;

means for generating timing signals having a frequency corresponding to the rate at which data are received by the memories;

means for generating clock signals having a frequency corresponding to the rate at which data are transmitted by the memories;

routing means for controlling the routing of the timing signals alternately to the first and second memories and of the clock signals alternately to the second and first memories;

means responsive to the first plurality of a group of timing signals for causing the routing means to reverse the routing of the timing signals and the clock signals; and means responsive to the clock signals for controlling the frequency of the means for generating the timing signals.

8. A system according to claim 19 wherein the first memory comprises:

a first random access memory and a first counter, the output of the first counter being arranged to address the location in the first random access memory in a predetermined sequence; and the second memory comprises a second random access memory and a second counter, the output of the second counter being arranged to address the locations in the second random access memory in a predetermined sequence.

* * * * *